(12) United States Patent
Kraft et al.

(10) Patent No.: US 8,703,692 B2
(45) Date of Patent: Apr. 22, 2014

(54) 7-(ALK-1'ENYL)-2H-BENZO[B][1,4] DIOXEPIN-3(4H)-ONES AND THEIR USE IN FRAGRANCE APPLICATIONS

(75) Inventors: Philip Kraft, Dübendorf (CH); Kasim Popaj, Dietikon (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 13/577,336

(22) PCT Filed: Feb. 9, 2011
(Under 37 CFR 1.47)

(86) PCT No.: PCT/EP2011/051871
§ 371 (c)(1),
(2), (4) Date: Aug. 6, 2012

(87) PCT Pub. No.: WO2011/098472
PCT Pub. Date: Aug. 18, 2011

(65) Prior Publication Data
US 2012/0309670 A1 Dec. 6, 2012

(30) Foreign Application Priority Data
Feb. 10, 2010 (GB) .................................. 1002216.8

(51) Int. Cl.
*A61Q 13/00* (2006.01)
(52) U.S. Cl.
USPC .......................................................... 512/12
(58) Field of Classification Search
USPC .......................................................... 512/12
See application file for complete search history.

(56) References Cited

FOREIGN PATENT DOCUMENTS

| DE | 102007055124 A1 | 5/2009 |
| EP | 1136481 A1 * | 9/2001 |
| EP | 1405851 A1 | 4/2004 |

OTHER PUBLICATIONS

English language abstract for DE 102007055124 published May 20, 2009.
GB Search Report for GB 1002216.8 dated May 21, 2010.
International Search Report for PCT/EP2011/051871 dated Apr. 1, 2011.
"Structure-Activity Relationship in the Domain of Odorants Having Marine Notes", J-M Gaudin, et al., Helvetica Chimica Acta, Verlag Helvatica Chimica, vol. 90, Jan. 1, 2007, pp. 1245-1265, XP002588169.
"Conception, Characterization and Correlation of New Marine Odorants", Philip Kraft, et al., European Journal of Organic Chemistry, vol., 2003, No. 19, Oct. 1, 2003, pp. 3735-3743, XP007917961.
Written Opinion of the International Searching Authority for PCT/EP2011/051871 dated Apr. 1, 2011.

* cited by examiner

*Primary Examiner* — Ling-Siu Choi
*Assistant Examiner* — Lanee Reuther
(74) *Attorney, Agent, or Firm* — Norris McLaughlin & Marcus PA

(57) ABSTRACT

A compound of the formula I

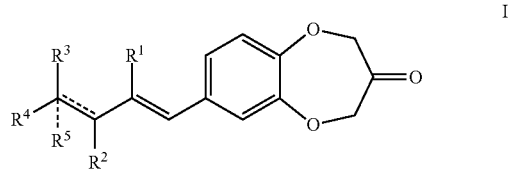

in which $R^1$ is H or methyl, $R^2$ is H, methyl or ethyl, $R^3$ and $R^4$ are independently hydrogen, methyl, ethyl, n-propyl or iso-propyl, and the dashed lines representing the alternative possibilities of there being present either an additional double bond or an additional group $R^5$, which is H or methyl.

The compounds possess a marine odor with sweet character, and are useful in fine and functional fragrances.

10 Claims, No Drawings

7-(ALK-1'ENYL)-2H-BENZO[B][1,4]DIOXEPIN-3(4H)-ONES AND THEIR USE IN FRAGRANCE APPLICATIONS

This is an application filed under 35 USC 371 of PCT/EP2011/051871.

This disclosure relates to substituted 7-(alk-1'-enyl)-2H-benzo[b][1,4]dioxepin-3(4H)-ones and to their use in fragrance applications.

Certain substituted 7-(alk-1'-enyl)-2H-benzo[b][1,4]dioxepin-3(4H)-ones are novel compounds. There is therefore provided a compound of the formula I

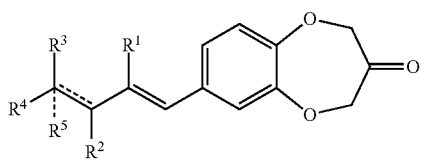

in which $R^1$ is H or methyl, $R^2$ is H, methyl or ethyl, $R^3$ and $R^4$ are independently hydrogen, methyl, ethyl, n-propyl or iso-propyl, and the dashed lines representing the alternative possibilities of there being present either an additional double bond or an additional group $R^5$, which is H or methyl.

The double bond (or, if present, both double bonds) may be in either the (E)- or in the (Z)-configuration, the (E)-configuration being in general more desirable for both for olfactory properties and ease of preparation.

Particular examples of compounds of Formula I include 7-(but-1'-enyl)-2H-benzo[b][1,4]dioxepin-3(4H)-one, 7-(4'-methylpent-1'-enyl)-2Hbenzo[b][1,4]dioxepin-3(4H)-one, 7-(3'-methylbut-1'-enyl)-2H-benzo[b][1,4]dioxepin-3(4H)-one, 7-(4',4'-dimethylpent-1'-enyl)-2H-benzo [b][1,4]-dioxepin-3(4H)-one, 7-(pent-1'-enyl)-2H-benzo[b][1,4]dioxepin-3(4H)-one, 7-(penta-1',3'-dienyl)-2H-benzo[b][1,4]dioxepin-3(4H)-one, 7-(2'-methylprop-1'-enyl)-2H-benzo[b][1,4]dioxepin-3(4H)-one, and 7-(3'-methylpent-1'-enyl)-2H-benzo[b][1,4]dioxepin-3(4H)-one, with either (E)- or (Z)-configured double bonds.

The compounds of formula I may conveniently be prepared from 7-(prop-1'-enyl)-2H-benzo[b][1,4]dioxepin-3(4H)-one by protection of the carbonyl function for instance as ketal, oxidative cleavage of the vinylic double bond for instance with ruthenium tetroxide generated in-situ, Grignard reactions on the resulting 3,4-dihydro-2H-benzo[b][1,4]dioxepine-7-carbaldehyde and subsequent dehydration.

The starting material, 7-(prop-1'-enyl)-2H-benzo[b][1,4]dioxepin-3(4H)-one can be prepared as illustrated in Example 1 from dimethyl 2,2'-(4-allyl-1,2-phenylene)-bis(oxy)diacetate by Dieckmann condensation with concomitant isomerisation of the double bond and subsequent saponification with decarboxylation. Dimethyl 2,2'-(4-allyl-1,2-phenylene)bis(oxy)diacetate is for instance accessible from eugenol according to the procedure described by P. Kraft and W. Eichenberger, *Eur. J. Org. Chem.* 2003, 3735-3743. Using thermodynamic conditions for the double-bond isomerisation, for instance by employing a reversible base such as potassium tert-butoxide leads to the (E)-configured isomer, while with other conditions the (E/Z)-ration could be adjusted.

The compounds of Formula I combine very intense marine notes with clean green-watery and aldehydic facets, and a sweet side of varying intensity in, for instance, the direction of vanilla or honey. This is surprising as, although the unstable aldehyde 3-oxo-3,4-dihydro-2H-benzo[b][1,4]dioxepine-7-carbaldehyde and the related nitro arene 7-nitro-2H-benzo[b][1,4]dioxepin-3(4H)-one possess a spicy, vanilla note (H. M. Hügel, B. Drevermann, A. R. Lingham, and P. J. Marriot, 'Marine Fragrance Chemistry' in 'Current Topics in Flavor and Fragrance Research' (Eds.: P. Kraft, K. A. D. Swift), Verlag Helvetica Chimica Acta, Zurich, and Wiley-VCH, Weinheim, 2008, p. 199-209), so far no odorant that possesses a marine character with additional vanillic-spicy aspects has been found, and the green-watery, aldehydic facet is also unusual as the known saturated compounds recall salty seawater, which sometimes has a negative, rather dirty connotation.

There is therefore also provided a method of providing to a fragrance application a marine odour comprising the addition to a fragrance application base of a compound of the general formula I, as hereinabove described.

In addition, the compounds of Formula I have low Odour Detection Thresholds (ODT), meaning that a relatively small quantity will provide an observable odour. In some cases, the ODTs are exceptionally low, and the combination of desirable odour quality and low ODT makes these compounds exceptionally desirable fragrance materials. Examples of compounds of Formula I and their corresponding ODTs are shown in the table below:

| Example No. | $R^1$ | $R^2$ | $R^3$ | $R^4$ | $R^5$ | Second double bond present | ODT (ng/L) |
|---|---|---|---|---|---|---|---|
| 1 | H | H | H | H | H | no | 0.00157 |
| 2 | H | H | $CH_3$ | $CH_3$ | H | no | 0.00025 |
| 3 | H | $CH_3$ | H | H | H | no | 0.015 |
| 4 | H | H | H | $CH_3$ | — | yes | 0.000141 |
| 5 | H | H | H | $CH_3$ | H | no | 0.00314 |
| 6 | H | H | $CH_3$ | $CH_3$ | $CH_3$ | no | 0.042 |
| 8 | H | $CH_3$ | $CH_3$ | H | H | no | 0.021 |
| 7 | $CH_3$ | H | H | H | H | no | 0.42 |

By 'fragrance application' is meant any composition for any use in which the presence of fragrant substances is required. These range from fine fragrances for personal use to fragrances added to commercial cosmetic, personal and household products, such as creams and lotions, soaps and shampoos, detergent powders, fabric softeners, surface cleaners and the like. A 'fragrance application base' is the fragrance application without fragrance.

Compound I may be used alone or blended with one or more of the many fragrance ingredients known to the art and readily available commercially from the major fragrance manufacturers. Non-limiting examples of such ingredients include ethereal oils and extracts, e.g. bergamot oil, grapefruit oil, jasmine absolute, lemon oil, mandarin oil, patchouli oil, vetiver or ylang-ylang oil;

alcohols, e.g. citronellol, dihydromycrenol, Ebanol™, eugenol, geraniol, Florol®, Super Muguet™, linalool, phenylethyl alcohol, Sandalore™, terpineol or Timberol™;

aldehydes and ketones, e.g. Adoxal™, Aldolone®, α-amylcinnamaldehyde, Azurone®, Cyclohexal™, α-damascone, β-damascenone, Florhydral™, Georgywood™, Hedione®, hydroxycitronellal, Iso E Super™, Isoraldeine™, lauryl aldehyde, maltol, methyl cedryl ketone, methyl ionone, 2-methylundecanal, Myraldene™, Transluzone®, undecanal, Vertofix™ or vanillin;

ether and acetals, e.g. Acetal E™, Ambrox™, geranyl methyl ether, rose oxide or Spirambrene™;

esters and lactones, e.g. allyl amyl glycolate, benzyl acetate, benzyl salicylate, cedryl acetate, Cyclogalbanate™, γ-decalactone, Helvetolide®, linalyl acetate, Serenolide®, γ-undecalactone, Verdox™ or vetivenyl acetate;

macro- and polycycles, e.g. ambrettolide, ethylene brassylate, Exaltolide™, Galaxolide® or Moxalone™; and heterocycles, e.g. isobutylchinoline.

In addition to their admixture with other fragrances, the compounds of formula I of the present invention may be admixed with one or more ingredients or excipients conventionally used in conjunction with fragrances in perfume compositions, for example carrier materials, and other auxiliary agents commonly used in the art, e.g., solvents such as dipropylene glycol (DPG), isopropyl myristate (IPM), and triethyl citrate (TEC).

The compounds of formula I may be used in a broad range of fragrance applications, for example, in any field of fine and functional perfumery, such as perfumes, household products, laundry products, body care products and cosmetics. Specific exemplary and non-limiting examples include as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant.

The compounds of formula I may can be employed in widely varying amounts, depending upon the specific application and on the nature and quantity of other fragrances. The proportions in which the compounds of the present invention are employed in application may vary within a large range of values and will depend upon the nature of the applications one intends to perfume, for example the nature of co-ingredients, and the particular effect that the perfumer seeks. Generally however, there may be employed up to about 3% by weight in fine fragrances, e.g. from about 0.01% by weight to about 3% by weight, and up to about 5% by weight based on the perfume composition in other fragrance applications, e.g. laundry products. However, these values are given only by way of example, since the experienced perfumer may also achieve effects or may create novel accords with lower or higher concentrations.

In the formulation of fragrance applications, there may also be used any of the known ingredients used in such applications, non-limiting examples including surfactants, solvents, pigments, dyestuffs, extenders, thickeners, rheology modifiers and the like.

The compounds of formula I may be employed into the fragrance application simply by directly mixing the perfume composition with a consumer product base, i.e., a combination of all of the other ingredients needed to make the desired product. Alternatively, the compounds may be used in entrapped form, in one or more of the available entrapment materials such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzymes, or the like, and then mixed with the application. The combination of the fragrance application ingredients, including compounds of formula I, may be in any desired order using any known method.

The disclosure will now be further described with reference to the following non-limiting examples. These examples are for the purpose of illustration only and it is understood that a person skilled in the art can make variations and modifications. The NMR data are given relative to internal $SiMe_4$ standard.

EXAMPLE 1

Preparation of (1'E)-7-(But-1'-enyl)-2H-benzo[b][1,4]dioxepin-3(4H)-one

At 0° C., a solution of dimethyl 2,2'-[(4-allyl-1,2-phenylene)bis(oxy)]diacetate (88.3 g, 300 mmol) in THF (400 mL) was added dropwise within 45 min. to a stirred suspension of potassium tert-butoxide (74.1 g, 660 mmol) in THF (400 mL), and the reaction mixture was stirred for 20 h under reflux. After cooling to room temperature, the resulting dark-brown solution was poured into ice/water (500 mL), acidified to pH 2 with aqueous 2N HCl and extracted with $CH_2Cl_2$ (3×300 mL). The combined organic extracts were dried ($Na_2SO_4$) and concentrated under reduced pressure on the rotary evaporator. The residue was taken up in EtOH (500 mL) and aqueous 2N HCl (500 mL) and the mixture was refluxed for another 20 h. The reaction mixture was poured into ice/water (600 mL), and extracted with $CH_2Cl_2$ (3×300 mL). The combined organic extracts were washed with water (300 mL), dried ($Na_2SO_4$), and the solvent was removed on the rotary evaporator under reduced pressure. The resulting residue was purified by chromatography on silica gel (pentane/ethyl acetate, 9:1, $R_f$ 0.27) to yield (1'E)-7-(prop-1'-enyl)-2H-benzo[b][1,4]dioxepin-3(4H)-one, which crystallized upon prolonged standing at room temperature; yield: 11.7 g (19%); colorless needles; mp 56-59° C. IR (neat): v=1263/1278 (s, v ring), 1043/1032/1118 (s, vC—O—C), 1501/1417/1438/1576 (s, vC=C ar), 1732 (s, vC=O), 881/903 (m, δ=C—H ar o.o.p., 1,2,4-tri), 962 (m, δC=C aliph) $cm^{-1}$. $^1H$ NMR (400 MHz, $CDCl_3$): δ=1.79 (dd, J=6.5, 1.5 Hz, 3 H, 3'-$H_3$), 4.62/4.63 (2s, 4 H, 2-, 4-$H_2$), 6.05 (dq, J=15.5, 6.5 Hz, 1 H, 2'-H), 6.22 (dq, J=15.5, 1.5 Hz, 1 H, 1'-H, (E)-configured), 6.83-6.90 (m, 3 H, 6-, 8-, 9-H). $^{13}C$ NMR (100 MHz, $CDCl_3$): δ=18.3 (q, C-3'), 75.6/75.7 (2t, C-2, -4), 117.9 (d, C-8), 120.9/121.3 (2d, C-6, -9), 125.7 (d, C-2'), 129.6 (d, C-1'), 134.3 (s, C-7), 147.1 (s, C-9a), 148.2 (s, C-5a), 204.5 (s, C-3). MS (EI, 70eV): m/z=205 (13) [(M+H)$^+$], 204 (100) [M$^+$], 175 (4) [M$^+$-CHO], 161 (7) [M$^+$-$C_2H_3O$], 120 (24) [$C_7H_4O_2^+$], 91 (58) [$C_7H_7^+$], 77 (2) [$C_6H_5^+$].

A solution of (1'E)-7-(prop-1'-enyl)-2H-benzo[b][1,4]dioxepin-3(4H)-one (10.6 g, 52.0 mmol), prepared according to the preceding working procedure, ethane-1,2-diol (9.96 g, 156 mmol) and concentrated $H_2SO_4$ (51 mg, 0.52 mmol) in toluene (200 mL) was stirred for 6 h under reflux in a Dean-Stark apparatus. The reaction mixture was allowed to cool to room temperature, taken up in $Et_2O$ (500 mL) and washed with saturated aqueous $NaHCO_3$ (2×100 mL). The combined organic extracts were dried ($Na_2SO_4$), and the solvent was evaporated on a rotary evaporator. The resulting residue was purified by chromatography on $Al_2O_3$ (pentane/ethyl acetate, 9:1, $R_f$ 0.35) to provide (1'E)-7-(prop-1'-enyl)-2,4-dihydrospiro[benzo[b][1,4]dioxepine-3,2'-[1,3]dioxolane] (8.27 g, 64%) as a slightly yellowish oil. IR (neat): v=1051 (s, vO—C—O), 1174 (s, vC—O ar), 1497 (s, vC=C ar), 876 (m, δC—H ar), 965 (m, δC=C aliph) $cm^{-1}$. $^1H$ NMR (400 MHz, $CDCl_3$): δ=1.84 (dd, J=6.5, 1.5 Hz, 3 H, 3'-$H_3$), 3.99 (s, 4 H, 2''-, 3''-$H_2$), 4.15/4.17 (2s, 4 H, 2-, 4-$H_2$), 6.10 (dq, J=15.5, 6.5 Hz, 1 H, 2'-H), 6.27 (dq, J=15.5, 1.5 Hz, 1 H, 1'-H, (E)- configured), 6.86-6.91 (m, 3 H, 6-, 8-, 9-H). $^{13}$C NMR (100 MHz, CDCl$_3$): δ=18.4 (q, C-3'), 64.6 (t, C-2",-3"), 73.6/73.7 (2t, C-2,-4), 108.1 (s, C-3), 117.7 (d, C-8), 120.6/120.7(2d, C-6,-9), 124.9 (d, C-2'), 129.8 (d, C-1'), 133.5 (s, C-7), 148.1 (s, C-9a), 149.2 (s, C-5a). MS (EI, 70 eV): m/z=249 (14) [(M+H)$^+$], 248 (100) [M$^+$], 233 (3) [M$^+$-CH$_3$], 176(11) [M$^+$-C$_3$H$_2$O$_2$], 86 (17) [C$_4$H$_6$O$_2^+$].

To a stirred solution of (1'E)-7-(prop-1'-enyl)-2,4-dihydrospiro[benzo[b][1,4]dioxepine-3,2'-[1,3]dioxolane] (7.45 g, 30.0 mmol), prepared according to the preceding working procedure, and ruthenium(III) chloride hydrate (311 mg, 1.50 mmol) in acetonitrile (60 mL), CH$_2$Cl$_2$ (30 mL) and H$_2$O (60 mL) was added portionwise at 0° C. sodium (meta)periodate (12.9 g, 60.0 mmol). The reaction mixture was stirred for 4 h at room temperature, taken up in H$_2$O (100 mL), and extracted with Et$_2$O (3×300 mL). The combined organic extracts were washed with 10% aqueous NaHSO$_3$ (2×100 mL), dried (Na$_2$SO$_4$) and evaporated on a rotary evaporator. The crude product was purified by flash chromatography on Al$_2$O$_3$ (pentane/ethyl acetate, 9:1, R$_f$0.28) to furnish 2,4-dihydrospiro{benzo[b][1,4]dioxepine-3,2"-[1,3]dioxolane}-7-carbaldehyde (2.63 g, 37%) as a slightly yellowish oil. IR (neat): ν=1032 (s, νO—C—O), 1689 (s, νC=O), 1172 (s, νC—O ar), 1493 (m, νC=C ar), 850 (m, δC—H ar), 945 (m, δC=C aliph) cm$^{-1}$. $^1$H NMR (400 MHz, CDCl$_3$): δ=1.84 (dd, J=6.5, 1.5 Hz, 3 H, 3'-H$_3$), 4.09 (s, 4 H, 2"-, 3"-H$_2$), 4.19/4.23 (2s, 4 H, 2-, 4-H$_2$), 7.05-7.48 (m, 3 H, 6-, 8-, 9-H).$^{13}$C NMR (100 MHz, CDCl$_3$): δ=64.7 (t, C2",-3"), 73.4/74.2 (2t, C-2,-4), 107.7 (s, C-3), 121.3/122.2 (2d, C-6,-9), 125.3(d, C-8), 131.9 (s, C-7), 149.5 (s, C-9a), 154.4 (s, C-5a), 190.4 (s, C-1'). MS (EI, 70 eV): m/z=237 (10) [(M+H)$^+$], 236 (100) [M$^+$], 163 (48) [M$^+$-C$_3$H$_5$O], 86 (82) [C$_4$H$_6$O$_2^+$].

A THF (20 mL) solution of 2,4-dihydrospiro{benzo[b][1,4]dioxepine-3,2"-[1,3]dioxolane}-7-carbaldehyde (2.36 g, 10 mmol), prepared according to the preceding working procedure, was added at 0° C. within 10 min. to a stirred solution of propyl magnesium chloride in THF (2 M, 7.50 mL, 15.0 mmol). Stirring was continued over night at room temperature, prior to quenching with saturated aqueous NH$_4$Cl (100 mL), and extraction of the product with Et$_2$O (3×300 mL). The combined organic layers were dried (Na$_2$SO$_4$), and concentrated in the rotary evaporator. The resulting residue was taken up in 50% aqueous H$_2$SO$_4$ (50 mL) and acetone (50 mL), and stirred for 6 h under reflux. The reaction mixture was poured into H$_2$O (100 mL), and the product extracted with Et$_2$O (3×300 mL). The combined organic extracts were washed with 5% aqueous NaHCO$_3$ (2×50 mL), dried (Na$_2$SO$_4$), and evaporated on the rotary evaporator. Purification of the residue by chromatography on silica gel (pentane/ethyl acetate, 95:5, R$_f$0.29) furnished (1'E)-7-(but-1'-enyl)-2H-benzo[b][1,4]dioxepin-3(4H)-one (590 mg, 27%) as a colorless odoriferous oil. IR (neat): ν=1263 (s, νC—O ar), 1043/1032 (s, νC—O aliph), 1499 (s, νC=C ar), 1733 (s, νC=O), 809 (m, δ=C—H ar) 965 (m, δC=C aliph) cm$^{-1}$. $^1$H NMR (400 MHz, CDCl$_3$): δ=1.08 (t, J=7.5 Hz, 3 H, 4'-H$_3$), 2.21 (quintd, J=7.5, 1.5 Hz, 2 H, 3'-H$_2$), 4.68/4.69 (2s, 4 H, 2-, 4-H$_2$), 6.16 (dt, J=15.5, 6.5 Hz, 1 H, 2'-H), 6.27 (dt, J=15.5, 1.5 Hz, 1 H, 1'-H, (E)-configured), 6.90-6.99 (m, 3 H, 6-, 8-, 9-H).$^{13}$C NMR (100 MHz, CDCl$_3$): δ=13.6 (q, C-4'), 25.9 (t, C-3'), 75.5/75.6 (2t, C-2,-4), 117.9 (d, C-8), 120.8/121.4(2d, C-6,-9), 127.3 (d, C-2'), 132.6 (d, C-1'), 134.3 (s, C-7), 147.1 (s, C-9a), 148.2(s, C-5a), 204.5 (s, C-3). MS (EI, 70 eV): m/z=219 (11) [(M+H)$^+$], 218 (100) [M$^+$], 203(38) [M$^+$-CH$_3$], 175 (16) [M$^+$-C$_2$H$_3$O], 91 (38) [C$_7$H$_7^+$], 77 (25) [C$_6$H$_5^+$].

Odour description: very powerful, watery-green, winy-fruity odour with slightly sweet vanillic facets.

Odour threshold: 0.00157 ng/L air.

EXAMPLE 2

Preparation of (1'E)-7-(4'-Methylpent-1'-enyl)-2H-benzo[b][1,4]dioxepin-3(4H)-one 2,4-dihydrospiro{benzo[b][1,4]dioxepine-3,2"-[1,3]dioxolane}-7-carbaldehyde (3.78 g, 16.0 mmol), prepared according to the working procedure in Example 1, was reacted with isopentyl magnesium chloride in THF (1 M, 24.0 mL, 24.0 mmol), and the crude product was refluxed in 50% aq. H$_2$SO$_4$/acetone (1:1, 100 mL). (1'E)-7-(4'-Methylpent-1'-enyl)-2H-benzo[b][1,4]dioxepin-3(4H)-one was obtained after standard workup and purification by chromatography on silica gel (pentane/ethyl acetate, 95:5, R$_f$0.35).

Yield: 434 mg (11%); colorless odoriferous oil. IR (neat): ν=1265 (s, νC—O ar), 1049/1033 (s, νC—O aliph), 1499 (s, νC=C ar), 1739 (s, νC=O), 965 (m, δC=C aliph) 819 (m, δ=C—H ar) cm$^{-1}$. $^1$H NMR (400 MHz, CDCl$_3$): δ=1.09 (d, J=6.5 Hz, 6 H, 4'-Me$_2$), 1.75(tsept, J=6.5, 6.5 Hz, 1 H, 4'-H), 2.07 (td, J=6.5, 1.0 Hz, 2 H, 3'-H$_2$), 4.70/4.71 (2s, 4H, 2-, 4-H$_2$), 6.11 (dt, J=15.5, 6.5 Hz, 1 H, 2'-H), 6.26 (dt, J=15.5, 1.5 Hz, 1 H, 1'-H, (E)-configured), 6.91-7.01 (m, 3 H, 6-, 8-, 9-H). $^{13}$C NMR (100 MHz, CDCl$_3$): δ=22.3 (q, 4'-Me$_2$), 28.5 (d, C-4'), 42.2 (t, C-3'), 75.5/75.6 (2t, C-2, -4), 117.9 (d, C-8), 120.8/121.4 (2d, C-6, -9), 129.3 (d, C-2'), 129.8 (d, C-1'), 134.3 (s, C-7), 147.1 (s, C-9a), 148.2(s, C-5a), 204.5 (s, C-3). MS (EI, 70 eV): m/z=247 (6) [(M$^+$+H)$^+$], 246 (32) [M$^+$], 231(3) [M$^+$-CH$_3$], 203 (100) [M$^+$-C$_2$H$_3$O], 91 (16) [C$_7$H$_7^+$], 77 (12) [C$_6$H$_5^+$].

Odour description: very powerful, watery, clean, transparent, fruity-aldehydic, slightly winy odour with somewhat sweet facets.

Odour threshold: 0.00025 ng/L air.

EXAMPLE 3

Preparation of (1'E)-7-(3'-Methylbut-1'-enyl)-2H-benzo[b][1,4]dioxepin-3(4H)-one As described for the preparation of (1'E)-7-(but-1'-enyl)-2H-benzo[b][1,4]dioxepin-3(4H)-one (Example 1), from 2,4-dihydrospiro{benzo[b][1,4]dioxepine-3,2"-[1,3]dioxolane}-7-carbaldehyde (5.11 g, 21.6 mmol), prepared according to the working procedure in Example 1, and isobutyl magnesium chloride in THF (1 M, 32 mL, 32 mmol) with refluxing of the crude product in 50% aq. H$_2$SO$_4$/acetone (1:1, 100 mL). (1'E)-7-(3'-Methylbut-1'-enyl)-2H-benzo[b][1,4]dioxepin-3(4H)-one was obtained after standard workup and purification by chromatography on silica gel (pentane/ethyl acetate, 95:5, R$_f$0.34). Yield: 301 mg (6%); colorless odoriferous oil. IR (neat): ν=1264 (s, νC—O ar), 1050/1033 (s, νC—O aliph), 1496 (s, νC=C ar), 1738 (s, νC=O), 965 (m, δC=C aliph) 807(m, δ=C—H ar) cm$^{-1}$. $^1$H NMR (400 MHz, CDCl$_3$): δ=1.08 (d, J=6.5 Hz, 6 H, 3'-Me$_2$), 2.44 (tsepd, J=6.5, 6.5 Hz, 1 H, 3'-H), 4.69/4.70 (2s, 4 H, 2-, 4-H$_2$), 6.08 (dd, J=16.0, 7.0 Hz, 1 H, 2'-H), 6.23 (dd, J=16.0, 1.0 Hz, 1 H, 1'-H, (E)-configured), 6.90-7.00 (m, 3H, 6-, 8-, 9-H). $^{13}$C NMR (100 MHz, CDCl$_3$): δ=22.4 (q, 3'-Me$_2$), 31.5 (d, C-3'), 75.6/75.7 (2t, C-2,-4), 118.0 (d, C-8), 120.9/121.5 (2d, C-6, -9), 125.5 (d, C-2'), 134.3 (d, C-1'), 138.0 (s, C-7), 147.1 (s, C-9a), 148.2 (s, C-5a), 204.5 (s, C-3). MS (EI, 70 eV): m/z=233 (9) [(M+H)$^+$], 232 (78) [M$^+$], 217 (100) [M$^+$-CH$_3$], 189 (116) [M$^+$-C$_2$H$_3$O], 91 (34) [C$_7$H$_7^+$], 77 (32) [C$_6$H$_5^+$].

Odour description: floral, watery marine odour with slightly fruity and sweet, honey-like facets.

Odour threshold: 0.015 ng/L air.

EXAMPLE 4

Preparation of (1'E,3'E)-7-(Penta-1',3'-dienyl)-2H-benzo[b][1,4]dioxepin-3(4H)-one As described for the preparation of (1'E)-7-(but-1'-enyl)-2H-benzo[b][1,4]dioxepin-3 (4H)-one (Example 1), from 2,4-dihydrospiro{benzo[b][1,4]dioxepine-3,2"-[1,3]dioxolane}-7-carbaldehyde (2.36 g, 10 mmol), prepared according to the working procedure in Example 1, and (E)-but-2-enyl magnesium chloride in THF (1 M, 15 mL, 15 mmol) with refluxing of the crude product in 50% aq. $H_2SO_4$/acetone (1:1, 100 mL). (1'E,3'E)-7-(Penta-1',3'-dienyl)-2H-benzo[b][1,4]dioxepin-3(4H)-one was obtained after standard workup and purification by chromatography on silica gel (pentane/ethyl acetate, 95:5, $R_f$ 0.30). Yield: 71.4 mg (3%); colorless odoriferous oil. IR (neat): ν=981 (s, δC=C aliph), 1265 (m, νC—O ar), 1045/1032 (m, νC—O aliph), 1733 (s, νC=O), 1499 (m, νC=C ar), 809 (m, δ=C—H ar) cm$^{-1}$. $^1$H NMR (400 MHz, CDCl$_3$): δ=1.81 (qd, J=7.0, 1.5 Hz, 3 H, 5'-H$_3$), 4.69/4.70 (2s, 4 H, 2-, 4-H$_2$), 5.81 (dq, J=15.0, 7.0 Hz, 1 H, 4'-H), 6.18 (ddq, J=15.0, 10.5, 1.5 Hz, 1 H, 3'-H, (E)-configured), 6.30 (d, J=15.5 Hz, 1H, 1'-H, (E)-configured), 6.63 (dd, J=15.5, 10.5 Hz, 1 H, 2'-H), 6.91-6.70 (m, 3 H, 6-, 8-, 9-H). $^{13}$C NMR (100 MHz, CDCl$_3$): δ=18.3 (q, C-5'), 75.6 (2t, C-2,-4), 117.9 (d, C-8), 120.9/121.6 (2d, C-6,-9), 128.2 (d, C-2'), 129.3 (d, C-3'), 130.4 (d, C-4'), 131.6 (d, C-1'), 133.9 (s, C-7), 147.3 (s, C-9a), 148.2 (s, C-5a), 204.4 (s, C-3). MS (EI, 70 eV): m/z=231 (12) [(M+H)$^+$], 230(100) [M$^+$], 215 (35) [M$^+$-CH$_3$], 187 (6) [M$^+$-C$_2$H$_3$O], 91 (37) [C$_7$H$_7^+$], 77 (26) [C$_6$H$_5^+$].

Odour description: green, watery marine odour with metallic and aldehydic aspects and some sweet touch.

Odour threshold: 0.000141 ng/L air.

EXAMPLE 5

Preparation of (1'E)-7-(Pent-1'-enyl)-2H-benzo[b][1,4]dioxepin-3(4H)-one

As described for the preparation of (1'E)-7-(but-1'-enyl)-2H-benzo[b][1,4]dioxepin-3(4H)-5 one (Example 1), from 2,4-dihydrospiro{benzo[b][1,4]dioxepine-3,2"-[1,3]dioxolane}-7-carbaldehyde (1.07 g, 4.50 mmol), prepared according to the working procedure in Example 1, and butyl magnesium chloride in THF (1 M, 6.75 mL, 6.75 mmol) with refluxing of the crude product in 50% aq. $H_2SO_4$/acetone (1:1, 100 mL). (1'E)-7-(Pent-1'-enyl)-2H-benzo[b][1,4]dioxepin-3(4H)-one was obtained after standard workup and purification by chromatography on silica gel (pentane/ethyl acetate, 95:5, $R_f$ 0.31). Yield: 71.3 mg (7%); colorless odoriferous oil. IR (neat): ν=1264 (s, νC—O ar), 1048/1033 (s, νC—O aliph), 1499 (s, νC=C ar), 1738 (s, νC=O), 962 (m, δC=C aliph), 826 (m, δ=C—H ar) cm$^{-1}$. $^1$H NMR (400 MHz, CDCl$_3$): δ=0.94 (t, J=7.5 Hz, 3 H, 5'-H$_3$), 1.47 (qt, J=7.5, 7.0 Hz, 2 H, 4'-H$_2$), 2.17 (td, J=7.0, 6.5 Hz, 2 H, 3'-H$_2$), 4.69/4.70 (2s, 4 H, 2-, 4-H$_2$), 6.12 (dt, J=15.5, 6.5 Hz, 1 H, 2'-H), 6.27 (dt, J=15.5, 1.5 Hz, 1 H, 1'-H, (E)-configured), 6.91-6.99 (m, 3 H, 6-, 8-, 9-H). $^{13}$C NMR (100 MHz, CDCl$_3$): δ=13.7 (q, C-5'), 22.5 (t, C-4'), 35.0 (t, C-3'), 75.5/75.6 (2t, C-2,-4), 117.9 (d, C-8), 120.8/121.4 (2d, C-6,-9), 128.4 (d, C-2'), 131.0 (d, C-1'), 134.3 (s, C-7), 147.1 (s, C-9a), 148.2 (s, C-5a), 204.5 (s, C-3). MS (EI, 70 eV): m/z=233 (8) [(M+H)$^+$], 232 (40) [M$^+$], 217 (4) [M$^+$-CH$_3$], 189 (11) [M$^+$-C$_2$H$_3$O], 91 (18) [C$_7$H$_7^+$], 77 (15) [C$_6$H$_5^+$].

Odour description: green, watery marine odour with metallic and aldehydic aspects and some sweet touch.

Odour threshold: 0.00314 ng/L air.

EXAMPLE 6

Preparation of (FE)-7-(4',4'-Dimethylpent-1'-enyl)-2H-benzo[b][1,4]-dioxepin-3(4H)-one As described for the preparation of (1'E)-7-(but-1'-enyl)-2H-benzo[b][1,4]dioxepin-3(4H)-one (Example 1), from 2,4-dihydrospiro{benzo[b][1,4]dioxepine-3,2"-[1,3]dioxolane}-7-carbaldehyde (2.84 g, 12 mmol), prepared according to the working procedure in Example 1, and 3,3-dimethylbutyl magnesium chloride in THF (1 M, 18.0 mL, 18.0 mmol) with refluxing of the crude product in 50% aq. $H_2SO_4$/acetone (1:1, 100 mL). (1'E)-7-(4',4'-Dimethylpent-1'-enyl)-2H-benzo[b][1,4]dioxepin-3(4H)-one was obtained after standard workup and purification by chromatography on silica gel (pentane/ethyl acetate, 95:5, $R_f$ 0.36). Yield: 251 mg (8%); colorless odoriferous oil. IR (neat): ν=1265 (s, νC—O ar), 1048/1032 (s, νC—O aliph), 1498 (s, νC=C ar), 1739 (s, νC=O), 965 (m, δC=C aliph) 807 (m, δ=C—H ar) cm$^{-1}$. $^1$H NMR (400 MHz, CDCl$_3$): δ=0.93 (s, 9 H, 4'-Me$_3$), 2.07 (td, J=6.5, 1.0 Hz, 2 H, 3'-H$_2$), 4.69/4.70 (2s, 4 H, 2-, 4-H$_2$), 6.17 (dt, J=15.5, 6.5 Hz, 1 H, 2'-H), 6.29 (dt, J=15.5, 1.5 Hz, 1 H, 1'-H, (E)-configured), 6.93-7.03 (m, 3 H, 6-, 8-, 9-H). $^{13}$C NMR (100 MHz, CDCl$_3$): δ=29.3 (q, 4'-Me$_3$), 31.8 (s, C-4'), 47.4 (t, C-3'), 75.5/75.6 (2t, C-2,-4), 119.0 (d, C-8), 120.9/121.5 (2d, C-6,-9), 128.2 (d, C-2'), 130.3 (d, C-1'), 134.2 (s, C-7), 147.1 (s, C-9a), 148.2 (s, C-5a), 204.5 (s, C-3). MS (EI, 70 eV): m/z=261 (5) [(M+H)$^+$], 260 (23) [M$^+$], 245 (9) [M$^+$-CH$_3$], 203 (100) [M$^+$-C$_4$H$_9$], 91 (12) [C$_7$H$_7^+$], 77 (8) [C$_6$H$_5^+$], 57 (60) [C$_4$H$_9^+$].

Odour description: floral, watery-green, marine, seashore, clean, with aldehydic and sweet aspects.

Odour threshold: 0.042 ng/L air.

EXAMPLE 7

Preparation of (1'E)-7-(2'-Methylprop-1'-enyl)-2H-benzo[b][1,4]dioxepin-3(4H)-one As described for the preparation of (1'E)-7-(but-1'-enyl)-2H-benzo[b][1,4]dioxepin-3 (4H)-one (Example 1), from 2,4-dihydrospiro{benzo[b][1,4]dioxepine-3,2"-[1,3]dioxolane}-7-carbaldehyde (3.31 g, 14 mmol), prepared according to the working procedure in Example 1, and isobutyl magnesium chloride in THF (1 M, 21.0 mL, 21 0 mmol) with refluxing of the crude product in 50% aq. $H_2SO_4$/acetone (1:1, 100 mL). 7-(2'-Methylprop-1'-enyl)-2H-benzo[b][1,4]dioxepin-3(4H)-one was obtained after standard workup and purification by chromatography on silica gel (pentane/ethyl acetate, 95:5, $R_f$ 0.32). Yield: 214 mg (7%); colorless oil. IR (neat): ν=1265 (s, νC—O ar), 1045/1032 (s, νC—O aliph), 1498 (s, νC=C ar), 1738 (s, νC=O), 810 (m, δ=C—H ar) 965 (m, δC=C aliph) cm$^{-1}$. $^1$H NMR (400 MHz, CDCl$_3$): δ=1.84 (d, J=1.5 Hz, 3 H, 1"-H$_3$), 1.88 (d, J=1.5 Hz, 3 H, 3'-H$_3$), 4.69/4.70(2s, 4 H, 2-, 4-H$_2$), 6.15 (s, 1 H, 1'-H), 6.81-6.94 (m, 3 H, 6-, 8-, 9-H). $^{13}$C NMR (100 MHz, CDCl$_3$): δ=19.4 (q, C-1"), 25.8 (q, C-3'), 75.5/75.6 (2t, C-2,-4), 120.4 (d, C-8), 120.8/123.7 (2d, C-6,-9), 124.3 (d, C-1'), 134.8 (s, C-7), 135.6 (s, C-2'), 146.3 (s, C-9a), 147.8 (s, C-5a), 204.6 (s, C-3). MS (EI, 70 eV): m/z=219 (12) [(M+H)$^+$], 218 (100) [M$^+$], 203 (29) [M$^+$-CH$_3$], 175 (15) [M$^+$-C$_2$H$_3$O], 91 (40) [C$_7$H$_7^+$], 77 (25) [C$_6$H$_5^+$].

Odour description: watery-green, floral, with sweet-fruity melon-like facets and some reminiscence to cyclamen aldehyde (2-methyl-3-(p-isopropylphenyl)propionaldehyde)

Odour threshold: 0.42 ng/L air. .

EXAMPLE 8

Preparation of (1'E)-7-(3'-Methylpent-1'-enyl)-2H-benzo[b][1,4]-dioxepin-3(4H)-one As described for the preparation of (1'E)-7-(but-1'-enyl)-2H-benzo[b][1,4]dioxepin-3(4H)-one (Example 1), from 2,4-dihydrospiro{benzo[b][1,4]dioxepine-3,2"-[1,3]diox-olane}-7-carbaldehyde (1.09 g, 4 6 mmol), prepared according to the working procedure in Example 1, and 2-methylbutylmagnesium chloride in THF (1 M, 7.0 mL, 7 0 mmol) with refluxing of the crude product in 50% aq. $H_2SO_4$/acetone (1:1, 100 mL). (1'E)-7-(3'-Methylpent-1'-enyl)-2H-benzo[b][1,4]-dioxepin-3(4H)-one was obtained after standard workup and purification by chromatography on silica gel (pentane/ethyl acetate, 95:5, $R_f$ 0.36). Yield: 60.5 mg (9%); colorless oil. IR (neat): v=1263 (s, vC—O ar), 1048/1032 (s, vC—O aliph), 1497 (s, vC=C ar), 1738 (s, vC=O), 810 (m, δ=C—H ar) 963 (m, δC=C aliph) cm$^{-1}$. $^1$H NMR (400 MHz, $CDCl_3$): δ=0.89 (t, J=7.0, Hz, 3 H, 5'-$H_3$), 1.06 (t, J=7.0, Hz, 3 H, 1"-$H_3$), 1.39 (dq, J=7.0, 7.0 Hz, 2 H, 4'-$H_2$), 2.18 (dtq, J=7.0, 7.0, 7.0 Hz, 1 H, 3'-H), 4.69/4.70 (2s, 4 H, 2-, 4-$H_2$), 5.99 (dq, J=16.0, 7.0 Hz, 1 H, 2'-H), 6.23 (d, J=16.0 Hz, 1 H, 1'-H, (E)-configured), 6.91-7.00 (m, 3 H, 6-, 8-, 9-H). $^{13}$C NMR (100 MHz, $CDCl_3$): δ=11.7 (q, C-5'), 20.1 (q, C-1") 29.7 (t, C-4'), 75.6/75.7 (2t, C-2,-4), 118.0 (d, C-8), 120.8/121.4 (2d, C-6,-9), 126.8 (d, C-1'), 134.3 (s, C-7), 136.7 (d, C-2'), 147.1 (s, C-9a), 148.2 (s, C-5a), 204.5 (s, C-3). MS (EI, 70 eV): m/z=247 (6) [(M+H)$^+$], 246 (32) [M$^+$], 231 (3) [M$^+$-$CH_3$], 203 (100) [M$^+$-$C_2H_3O$], 91 (16) [$C_7H_7^+$], 77 (12) [$C_6H_5^+$].

Odour description: watery-green, floral-aldehydic, marine, with sweet aspects of algae and eggnog.
Odour threshold: 0.021 ng/L air.

EXAMPLE 9

Perfume Formulation for Use in Shower Gels

Two perfume formulations were prepared, one (A) with the compound of Example 8, the other (B) without.

| Compound/Ingredient | parts by weight $^{1}/_{1000}$ (A) | (B) |
|---|---|---|
| benzyl salicylate | 200.0 | 190.0 |
| Cashmeran ™ (1,2,3,5,6-hexahydro-1,1,2,3,3-pentamethyl-4H-inden-4-one) | 5.0 | 5.0 |
| Citronellol (extra pure quality) | 60.0 | 60.0 |
| Cristalone ™ (ethyl safranate, 2,2,6-trimethylcyclohexa-1,3-diene-1-carboxylic acid ethyl ester) | 10.0 | 10.0 |
| ethyl linalool | 120.0 | 120.0 |
| ethyl 2-methylbutyrate | 3.0 | 3.0 |
| Freskomenthe ™ (2-sec-Butyl cyclohexanone) | 30.0 | 30.0 |
| Hedione ™ (methyl 2-(3'-oxo-2'-pentylcyclopentyl)-acetate) | 20.0 | 120.0 |
| hexyl acetate | 30.0 | 30.0 |
| Galaxolide ™ S ((4S)-1,3,4,6,7,8-hexahydro-4,6,6,7,8,8-hexamethylcyclopenta[g]-2-benzopyran) | 100.0 | 100.0 |
| maltyl isobutyrate | 1.0 | 1.0 |
| Isoraldeine ™ 70 (2-methyl-4-(2,6,6-trimethyl-2-cyclohexen-1-yl)-3-buten-2-one and isomers) | 30.0 | 30.0 |
| Lemonile ™ (3,7-dimethyl-2(3),6-nonadienenitrile) | 4.0 | 4.0 |
| Manzanate ™ (ethyl 2-methylvalerate) | 6.0 | 6.0 |
| Mefrosol ™ (3-methyl-5-phenylpentanol) | 180.0 | 180.0 |
| Neocaspirene ™ (2,7-dimethyl-10(1'-methylethyl)-1-oxaspiro [4.5]deca-3,6-diene) | 6.0 | 6.0 |
| Petalia ™ (cyclohexylidene-o-tolylacetonitrile) | 70.0 | 70.0 |
| Pharaone ™10%/DPG (dipropylene glycol) | 6.0 | 6.0 |
| Radjanol ™ (2-ethyl-4-(2',2',3'-trimethylcyclopent-3'-enyl)but-2-en-1-ol) | 15.0 | 15.0 |
| rose oxide | 3.0 | 3.0 |
| Zinarine ™ (2-(2',4'-dimethylcyclohexyl)pyridine) | 1.0 | 1.0 |
| (1'E)-7-(3'-methylpent-1'-enyl)-2H-benzo[b][1,4]-dioxepin-3(4H)-one (Example 8) @ 10% DPG | 0.0 | 10.0 |
| Total | 1000 | 1000 |

This perfumery formula intended for application @1% in shower gel, presents a fruity floral accord, with a dominant red berry note and some soft musky woody undertones. he (1'E)-7-(3'-methylpent-'-enyl)-2H-benzo[b][1,4]-dioxepin-3(4H)-one (Example 8) lifts up the fresh fruity top note, reinforces the natural feeling and conveys a clean watery dimension to the accord.

EXAMPLE 10

Hesperidic, Woody, Musky, Floral Feminine Fine Fragrance

| Compound/Ingredient | parts by weight $^{1}/_{1000}$ |
|---|---|
| Ambrofix ™ (dodecahydro-3a,6,6,9a-tetramemylnaphthol-[2,1-b]furan) | 2.4 |
| benzyl salicylate | 119.0 |
| citronellyl acetate | 11.9 |
| citrus essence (Italy) | 53.6 |
| cyclohexal | 23.8 |
| dipropylene glycol (DPG) | 5.3 |
| ethylene brassylate | 95.2 |
| Gardenol ™ (methyl phenyl carbinyl acetate) | 6.0 |
| Georgywood ™ (2-acetyl-1,2,3,4,5,6,7,8-octahydro-1,2,8,8-tetramethylnaphthalene) | 297.6 |
| grapefruit essence | 83.3 |
| Hedione ™ (methyl 2-(3'-oxo-2'-pentylcyclopentyl)-acetate) | 119.0 |
| cis-3-hexenol | 3.6 |
| cis-3-hexenyl salicylate | 17.9 |
| linalyl acetate | 53.6 |
| orange oil (Brazil) | 29.8 |
| Pepperwood ™ (3,7-dimethylocta-1,6-dien-3-yl dimethylcarbamate) | 23.8 |
| Pomarose ™ ((2E,5E/Z)-5,6,7-trimethylocta-2,5-dien-4-one) | 0.4 |
| Serenolide ™ (2-(1'-(3",3"-dimethylcyclohexyl)ethoxy)-2-methyl-propyl cyclopropanecarboxylate) | 53.6 |
| compound of the general formula I specified below | 0.2 |
| Total | 1000 |

Addition 0.2% of a compound of the general formula I provides lift, volume and a marine character to this hesperidic, woody, musky, floral feminine fine fragrance formulation. It increases the bloom and the freshness and induces an aquatic transparency. In addition, depending on the specific compound, unique signatures can be created.

If (1'E)-7-(4'-methylpent-1'-enyl)-2H-benzo[b][1,4]diox-epin-3(4H)-one (Example 2) or 7-(2'-methylprop-1'-enyl)-

2H-benzo[b][1,4]dioxepin-3(4H)-one (Example 7) is employed, the juiciness, and the overall fruity character of the composition is in addition enhanced. These two materials combine especially well with the green-floral heart around the Hedione-hexenol accord, emphasize it, and bringing it to the fore.

If (1'E)-7-(4',4'-dimethylpent-1'-enyl)-2H-benzo [b][1,4]-dioxepin-3(4H)-one (Example 6) is employed, the woody-ambery fond of the composition is enhanced, while its marine-aquatic character leads into the green-floral part, and provides the overall fragance with radiance and clarity.

When (1'E)-7-(3'-methylbut-1'-enyl)-2H-benzo [b][1,4] dioxepin-3(4H)-one (Example 3), (1'E ,3'E)-7-(penta-1',3'-dienyl)-2H-benzo[b][1,4]dioxepin-3(4H)-one (Example 4) or (1'E)-7-(pent-1'-enyl)-2H-benzo [b][1,4]dioxepin-3(4H)-one (Example 5) is employed, the musky-floral character of the composition is in addition modified and stressed by a specific metallic-aldehydic freshness. When (1'E)-7-(but-1'-enyl)-2H-benzo[b][1,4]dioxepin-3(4H)-one (Example 1) or (1'E)-7-(3'-methylpent-1'-enyl)-2H-benzo [b][1,4]-dioxepin-3(4H)-one (Example 8) are being used, a certain sweetness is added to the soft woody-musky side of the fragrance, in addition to the marine character and the aquatic transparency that all the compounds of the general formula provide.

The invention claimed is
1. A compound of the formula I

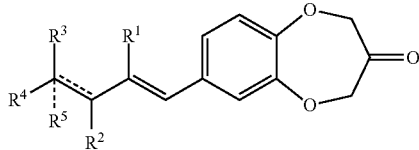

I in which $R^1$ is H or methyl, $R^2$ is H, methyl or ethyl, $R^3$ and $R^4$ are independently hydrogen, methyl, ethyl, n-propyl or iso-propyl, and the dashed lines representing the alternative possibilities of there being present either an additional double bond or an additional group $R^5$, which is H or methyl.

2. A compound according to claim 1, in which $R^1$ is hydrogen, and the optional double bond is absent.

3. A compound according to claim 2, in which the double bond is in the (E)-configuration.

4. A compound according to claim 1, in which the optional double bond is present.

5. A compound according to claim 4, in which at least one double bond is in the (E)-configuration.

6. A compound according to claim 1, wherein the compound of formula I is selected from the group consisting of:
7-(but-1'-enyl)-2H-benzo [b][1,4]dioxepin-3(4H)-one,
7-(4'-methylpent-1'-enyl)-2H-benzo [b][1,4]dioxepin-3(4H)-one,
7-(3'-methylbut-1'-enyl)-2H-benzo [b][1,4]dioxepin-3(4H)-one,
7-(4',4'-dimethylpent-1'-enyl)-2H-benzo [b][1,4]-dioxepin-3(4H)-one,
7-(pent-1'-enyl)-2H-benzo [b][1,4]dioxepin-3(4H)-one,
7-(penta-1',3'-dienyl)-2H-benzo[b][1,4]dioxepin-3(4H)-one,
7-(2'-methylprop-1'-enyl)-2H-benzo[b][1,4]dioxepin-3(4H)-one, and
7-(3'-methylpent-1'-enyl)-2H-benzo [b][1,4]dioxepin-3(4H)-one,
wherein any of the foregoing compounds comprise either (E)- or (Z)-configured double bonds.

7. A method of providing to a fragrance application a marine, green-watery odour with sweet character, the method comprising the step of:
providing within the fragrance application a compound of the general formula I according to claim 1.

8. An odorant compound according to the compound of formula I according to claim 1.

9. A fragrance application comprising a fragrance application base and at least one compound of formula I according to claim 1.

10. A method for improving, enhancing, or modifying a fragrance application, comprising the step of:
adding to the fragrance application an improving, enhancing or modifying proportion of at least one compound of formula I according to claim 1.

* * * * *